(12) United States Patent
Smith et al.

(10) Patent No.: US 10,836,639 B1
(45) Date of Patent: Nov. 17, 2020

(54) AIR QUALITY MEASUREMENT SYSTEM

(71) Applicant: Air Stations LLC/Elevated Analytics LLC Joint Venture, Tulsa, OK (US)

(72) Inventors: Joseph D. Smith, Rolla, MO (US); Robert E. Jackson, Mapleton, UT (US); Zachary P. Smith, Broken Arrow, OK (US)

(73) Assignee: AIR STATIONS LLC/ELEVATED ANALYTICS LLC JOINT VENTURE, Tulsa, OK (US)

( * ) Notice: Subject to any disclaimer, the term of this patent is extended or adjusted under 35 U.S.C. 154(b) by 222 days.

(21) Appl. No.: 15/794,064

(22) Filed: Oct. 26, 2017

Related U.S. Application Data

(60) Provisional application No. 62/413,107, filed on Oct. 26, 2016.

(51) Int. Cl.
| | | |
|---|---|---|
| *G01K 1/00* | (2006.01) | |
| *G01K 13/00* | (2006.01) | |
| *G01K 7/00* | (2006.01) | |
| *G01K 11/00* | (2006.01) | |
| *C01B 32/174* | (2017.01) | |

(Continued)

(52) U.S. Cl.
CPC ............ *C01B 32/174* (2017.08); *B82Y 15/00* (2013.01); *B82Y 30/00* (2013.01); *G01K 7/343* (2013.01); *G01L 1/205* (2013.01); *G01N 33/551* (2013.01); *G01K 2211/00* (2013.01); *H01B 1/04* (2013.01); *H01B 1/24* (2013.01)

(58) Field of Classification Search
USPC ........ 374/141, 208, 143, 166; 977/902, 953, 977/955
See application file for complete search history.

(56) References Cited

U.S. PATENT DOCUMENTS

| | | |
|---|---|---|
| 5,831,876 A | 11/1998 | Orr et al. |
| 6,085,576 A | 7/2000 | Sunshine et al. |

(Continued)

FOREIGN PATENT DOCUMENTS

| | | |
|---|---|---|
| CN | 202083808 | 12/2011 |
| CN | 103728198 | 4/2014 |

(Continued)

OTHER PUBLICATIONS

David T. Allen, Vincent M. Torres, TCEQ 2010 Flare Study Final Report, Texas Commission on Environmental Quality, The University of Texas at Austin the Center for Energy and Environmental Resources, Aug. 1, 2011.

(Continued)

*Primary Examiner* — Mirellys Jagan
(74) *Attorney, Agent, or Firm* — Head, Johnson, Kachigian & Wilkinson, PC

(57) ABSTRACT

An air quality measurement system to monitor atmospheric properties at various locations, elevations, and times. The system includes an unmanned aerial vehicle having at least one carbon nanotube sensor for monitoring atmospheric air quality. Measurements of temperature, pressure, moisture, and gas species are obtained. A monitor mounted on the aerial vehicle is in communication with the sensor. A transmitter mounted on the aerial vehicle is in communication with the monitor for transmission of measurement data to a ground position controller.

15 Claims, 3 Drawing Sheets

(51) Int. Cl.
*G01K 7/34* (2006.01)
*G01L 1/20* (2006.01)
*B82Y 15/00* (2011.01)
*G01N 33/551* (2006.01)
*B82Y 30/00* (2011.01)
*H01B 1/04* (2006.01)
*H01B 1/24* (2006.01)

(56) References Cited

U.S. PATENT DOCUMENTS

| | | |
|---|---|---|
| 6,941,193 B2 | 9/2005 | Frecska et al. |
| 7,259,357 B2 | 8/2007 | Walker |
| 7,360,461 B2 | 4/2008 | Desrochers et al. |
| 8,294,008 B2 * | 10/2012 | Cole ............... B82Y 15/00 204/400 |
| 8,529,124 B2 * | 9/2013 | Kaul ............... G01N 27/127 374/1 |
| 8,765,488 B2 | 7/2014 | Strano et al. |
| 8,955,367 B2 | 2/2015 | Gouma et al. |
| 9,199,725 B2 | 12/2015 | Yelland et al. |
| 9,311,805 B2 | 4/2016 | Zishaan |
| 9,405,533 B2 | 8/2016 | Bouzas et al. |
| 9,453,814 B2 | 9/2016 | Tran |
| 9,536,149 B1 | 1/2017 | Cesarano |
| 9,551,616 B2 | 1/2017 | McQuilkin et al. |
| 2005/0139363 A1 | 6/2005 | Thomas |
| 2005/0262943 A1 | 12/2005 | Claydon et al. |
| 2006/0000259 A1 | 1/2006 | Rothschild et al. |
| 2007/0005267 A1 | 1/2007 | Li |
| 2007/0232950 A1 | 10/2007 | West |
| 2007/0292896 A1 * | 12/2007 | Strano ............... B82Y 15/00 435/7.9 |
| 2008/0034842 A1 * | 2/2008 | Lee ............... G01N 27/127 73/31.05 |
| 2009/0084162 A1 * | 4/2009 | Besnard ............ G01N 27/127 73/31.06 |
| 2009/0100458 A1 | 4/2009 | Chan et al. |
| 2010/0225493 A1 | 9/2010 | Zishaan |
| 2011/0051775 A1 | 3/2011 | Ivanov et al. |
| 2011/0174054 A1 | 7/2011 | Lynn |
| 2012/0015621 A1 | 1/2012 | Cerny et al. |
| 2012/0111093 A1 * | 5/2012 | Brahim ............... B82Y 15/00 73/23.35 |
| 2012/0326093 A1 | 12/2012 | Landorf |
| 2014/0138588 A1 | 5/2014 | Landorf et al. |
| 2014/0315323 A1 | 10/2014 | Pereira et al. |
| 2015/0233856 A1 * | 8/2015 | Samuilov ............ G01K 13/00 702/65 |
| 2015/0323482 A1 * | 11/2015 | Shimoyama ....... G01N 27/125 73/31.06 |
| 2016/0025517 A1 | 1/2016 | Giedd et al. |
| 2016/0054258 A1 * | 2/2016 | Nicholas ............ B82Y 30/00 205/794.5 |
| 2016/0167791 A1 * | 6/2016 | Roach ............... C25D 5/16 219/546 |
| 2017/0016850 A1 | 1/2017 | Tran |
| 2018/0022451 A1 * | 1/2018 | Lim ............... B64C 27/08 244/17.23 |
| 2018/0313775 A1 * | 11/2018 | Iftime ............... G01N 33/0009 |

FOREIGN PATENT DOCUMENTS

| | | |
|---|---|---|
| CN | 104458905 | 3/2015 |
| CN | 104583764 | 4/2015 |
| CN | 104713922 | 6/2015 |
| CN | 204557260 | 8/2015 |
| CN | 204719251 | 10/2015 |
| CN | 105051658 | 11/2015 |
| CN | 204901580 U | 12/2015 |
| CN | M4964476 | 1/2016 |
| CN | 106168617 | 11/2016 |
| EP | 527307 | 2/1993 |
| EP | 2048854 | 4/2009 |
| EP | 2304427 | 4/2011 |
| EP | 2699888 | 2/2014 |
| EP | 3092540 | 11/2016 |
| EP | 2761285 | 2/2017 |
| EP | 3183722 | 6/2017 |
| KR | 1020110077040 | 7/2011 |
| KR | 1020150112118 | 10/2015 |
| NZ | 566000 | 4/2011 |
| WO | 2009013508 | 1/2009 |
| WO | 2010013023 | 2/2010 |
| WO | 2010037425 | 4/2010 |
| WO | 2012023136 | 2/2012 |
| WO | 2012177975 | 12/2012 |
| WO | 2013112287 | 8/2013 |
| WO | 2014081331 | 5/2014 |
| WO | 2016145300 | 9/2016 |
| WO | 2016147098 | 9/2016 |
| WO | 2017068499 | 4/2017 |

OTHER PUBLICATIONS

Kelsey D. Atherton, NASA Now Has a Drone That Can Sniff Out Dangerous Gas Leaks, Popular Science, Mar. 30, 2016.
Black Swift Technologies, Commercial & Scientific Unmanned Aircraft, http://blackswifttech.com/, 2017.
Christophe Buchler, Magali Rollin, User-Friendly Composites That Take the Heat, JEC Magazine, Nov.-Dec. 2009, p. 33-35, No. 53.
Shay Castle, Boulder's Black Swift Wins NASA Deal for Drone-Based Volcano Tracking, Boulder Daily Camera, May 3, 2017.
Dennis Fandrich, Mark Iden, Drones with Innovative Gas Detection Sensors Usher in a New Pipeline Inspection Era, Pipeline Technology Journal, Mar. 30, 2016.
Luke Geiver, GE Unveils Drone, Sensor Package Aimed at Detecting Fugitive Gas, UAS Magazine, Oct. 12, 2016.
Dr. Felipe Gonzalez, Miguel A. Alvarado Molina, Tommaso Villa, UAVs for Gas Plume and Ultrafine Particles Monitoring, Mining and Energy in 2025 & Beyond, May 26, 2016.
GPS World Staff, Inspector Gadget: Drones Could Solve Gas-Leak Detection Issue, GPS World, Mar. 5, 2016.
Matthew R. Johnson, Robin W. Devillers, Kevin A. Thomson, Quantitative Field Measurement of Soot Emission from a Large Gas Flare Using Sky-LOSA, Environmental Science and Technology, 2011, vol. 45. p. 345-350.
Matthew R. Johnson, Robin W. Devillers, Chen Yang, Keven A. Thomson, Sky-Scattered Solar Radiation Based Plume Transmissivity Measurement to Quantify Soot Emissions from Flares, Enviromental Science and Technology, Sep. 23, 2010, vol. 44, No. 21, p. 8196-8202.
R. Colin Johnson, Gas Sensors Penetrate Smartphones, EE Times, Nov. 5, 2015, AspenCore.
Marc McDaniel, Flare Efficiency Study, Engineering-Science, Inc., Jul. 1983.
James D.N. McEwen, Matthew R. Johnson, Black Carbon Particulate Matter Emission Factors for Buoyancy-Driven Associated Gas Flares, Journal of the Air & Waste Management Association, Jan. 20, 2012.
Mariella Moon, GE Made an Oilfield Drone That Can Sniff Out Gas Leaks, Engadget, Oct. 9, 2016.
Rhett Morgan, Zeeco Calls Its New Direct Flare-Monitoring Technology a Game-Changer, Tulsa World, Jul. 28, 2017.
NASA, Carbon Nanotube Sensors for Gas Detection, Ames Technology Capabilities and Facilities, NASA.gov, Jul. 18, 2016.
NASA, NASA Flies Dragon Eye Unmanned Aircraft Into Volcanic Plume, www.nasa.gov, Apr. 2, 2013.
NASA, Mini NASA Methane Sensor Makes Successful Flight Test, Jet Propulsion Laboratory California Institute of Technology, Mar. 28, 2016.
National Aeronautics and Space Administratioin (NASA), NASA Ames Scientist Develops Cell Phone chemical Sensor, NASA.gov, Oct. 30, 2009.
Mark Scott, Energy Giants Turn to Drones and Sensors in New Embrace of the Digital World, The New York Times, Nov. 3, 2016, The New York Times Company.

(56) References Cited

OTHER PUBLICATIONS

URS Corporation, Passive FTIR Phase I Testing of Simulated and Controlled Flare Systems Final Report, Texas Commission on Environmental Quality, Jun. 2004.
U.S. EPA Office of Air Quality Planning and Standards (OAQPS), Parameters for Properly Designed and Operated Flares, Report for Flare Review Panel, Apr. 2012.
VTT Technical Research Centre of Finland, Scientists Developed a Miniature Gas Sensor for Mobile Devices—Applications from Monitoring Air Quality to Healthcare & Wellness, vttresearch.com, Aug. 13, 2015.

* cited by examiner

AIR QUALITY MEASUREMENT SYSTEM

CROSS REFERENCE

This application claims priority to and the benefit of U.S. Provisional Patent Application Ser. No. 62/413,107, filed Oct. 26, 2016, which is incorporated herein in its entirety by reference.

BACKGROUND OF THE INVENTION

Field of the Invention

The present invention relates generally to a system to measure atmospheric air quality with unmanned aerial vehicles having advanced sensors in order to monitor atmospheric properties at various locations and times. In particular, the present invention is directed to an air quality measurement system capable of identifying and quantifying emissions from industrial and commercial sources.

Description of the Related Art

Emissions from industrial and commercial sources are generated in a variety of ways. For example, flaring is used to oxidize flammable unwanted gases. Oxidation can reduce emissions of a principal component, methane, but can create other emissions.

It is desirable to identify and quantify emissions from industrial and commercial sources. Identifying and quantifying emissions is desirable to rate combustion efficiency and waste emissions. For example, determining temperatures and species concentrations of key compounds in a plume and atmosphere above large flames, such as flares, has long been desired but has generally been impractical due to the difficulty of getting a closed control volume for the combustion products as can be done with stack testing.

The flares themselves may be at remote and elevated locations. Additional challenges to identifying and quantifying emissions include atmospheric wind.

At the same time, work has been done to attempt to characterize flare performance in terms of combustion efficiency and emissions, such as the extensive 1983 study sponsored by the Chemical Manufacturers Association (CMA). See "User-Friendly Composites That Take The Heat" by Christophe Bulcher and Dr. Magali Rollin, JEC Composites Magazine, No. 53 November-December 2009); the Texas Commission on Environmental Quality's 2010 Study, "TCEQ 2010 Flare Study Final Report," prepared by D. T. Allen and V. M. Torres at The University of Texas at Austin The Center for Energy and Environmental Resources, Austin, Tex., August 2011; as well as more recent research, such as black carbon (BC) emission research by Johnson et al., "Black Carbon Particulate Matter Emission Factors for Buoyancy-Driven Associated Gas Flares," J. D. McEwen and M. R. Johnson, *Journal of the Air & Waste Management Association*, 62:3, pp. 307-321, 2012.

New techniques are being developed, such as Johnson's SKY-LOSA optical technique for black carbon (BC). See M. R. Johnson, R. W. Devillers and K. A. Thomson, "Quantitative Field Measurement of Soot Emission from a Large Gas Flare Using Sky-LOSA," *Environ. Sci. Technol.*, Vol. 45, No. 1, pp. 345-350, 2011; passive FTIR (PFTIR), URS Corporation, "Passive FTIR Phase I Testing of Simulated and Controlled Flare Systems FINAL REPORT," URS Corporation, Houston, Tex., 2004; and a unique sample probe system developed by Aerodyne Research, Inc. (ARI), which was used in the TCEQ study. These tests, particularly the 1983 CMA studies, have been done for some limited flares using large cranes and booms holding sensors placed over the flares. These types of measurements are usually limited to just one single key area above the flare in order to determine macro-properties of the plume, such as destruction and combustion efficiencies. As useful as this data has been, it has limited the understanding of what is taking place inside the plume and the dispersion of the plume in the atmosphere.

To gain a better understanding of the actual combustion performance of flares, accurate measurement of properties in the plume is most advantageous. The PFLIR and SKY-LOSA techniques offer promise for obtaining key data in the plume but costs for the equipment and setup on site are currently too prohibitive to do testing on a regular basis. The current invention is affordable and offers the capability to measure a wide range of species concentrations, as well as temperature and pressure, with costs that are more likely to make routine testing an affordable option.

Being able to monitor the dispersion of gases from accidental leaks or spills in real time, instead of just set locations downstream, can provide valuable insight into the dispersion of the gas plume and provide more accurate warnings for downstream areas that will be affected. The present invention provides a small mobile unmanned aerial vehicle that could make rapid multiple measurements of the contents of plumes.

Existing sensors to determine properties of gases and liquids include gas chromatograph and mass spectrometry sensors.

The development of lightweight sensors has shown great promise for reducing the size, cost, and weight of sensors that can determine various properties in gases and liquids. For example, in a 2008 NASA government report, nanotechnology based chemical sensors were disclosed. Each sensor in an array consists of a nanostructure and a transducer. See also hia N. Ivanov, "Carbon Nanotube Temperature and Pressure Sensors", U.S. Patent Publication No. 2011/0051775 A1, 3 Mar. 2011; B. P. B. Michael S. Strano, "Sensors Employing Single-Walled Carbon Nanotubes", U.S. Pat. No. 8,765,488 B2, 1 Jul. 2014; and C. Landorf, "Highly Soluble Carbon Nanotubes With Enhanced Conductivity," Patent Publication No. WO2012/177975 A1, 27 Dec. 2012.

At the same time, developments in unmanned aerial vehicles (UAVs) have led to increased capabilities in UAVs at reduced costs. The present invention extends these developments by utilizing lightweight and mechanically stable materials which are temperature resistant and chemical resistant for UAVs.

Combining these technological developments together form the basis for the current invention, an unmanned aerial vehicle with lightweight sensors mounted onboard to monitor properties in aerial plumes, such as temperature, pressure, moisture, and species concentrations of various gases or compounds of interest, such as CO, $CO_2$, NOx, SOx, $CH_4$, and other hydrocarbon gases.

By obtaining multiple measurements at different times and at different locations and different elevations, the performance and efficiency of an industrial process can be evaluated and even improved.

By obtaining multiple measurements at different times and at different locations and at different elevations, emissions from industrial and commercial sources can be evaluated.

By obtaining multiple measurements at different times and at different locations, the presence and direction of movement of emissions can be predicted.

Based on the foregoing, it is desirable to provide a system capable of identifying and quantifying emissions from industrial and commercial sources.

It is further desirable to provide a system to measure atmospheric air quality to monitor atmospheric properties at various locations, elevations, and times.

It is further desirable to provide a system to utilize atmospheric air measurements to predict future movement or dispersion of emissions.

SUMMARY OF THE INVENTION

In general, the present invention is directed to an air quality measurement system. Lightweight sensors capable of measuring temperatures, pressures and moisture content, as well as species concentrations of gases or compounds, are mounted on an unmanned, low altitude aerial vehicle. The unmanned aerial vehicle (UAV) may take different forms and includes a communications transmitter and an antenna.

The UAV is constructed of high temperature glass-ceramic matrices and inorganic polymers, which are both temperature and chemical resistant.

A plurality of electrically interconnected carbon nanotubes are mounted on a rigid substrate. A power source provides a substantially constant current to the electrically interconnected carbon nanotubes. The resistance or capacitance of the electrically interconnected carbon nanotubes is correlated to atmospheric temperature and/or pressure.

Additionally, and separately, relative humidity measurements are obtained from sensors. In another aspect of the invention, sensors capable of measuring gas compounds or species are mounted on the UAV.

Multiple atmospheric air measurements are taken with the sensors at multiple different times at multiple different locations. The sensor readings in the form of data are transmitted from a transmitter on the unmanned aerial vehicle to a ground position controller. The ground position controller includes a database or is connected to a database. The contour of the plume, the dispersion of the plume, and movement of the plume is determined.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

Figure 1:
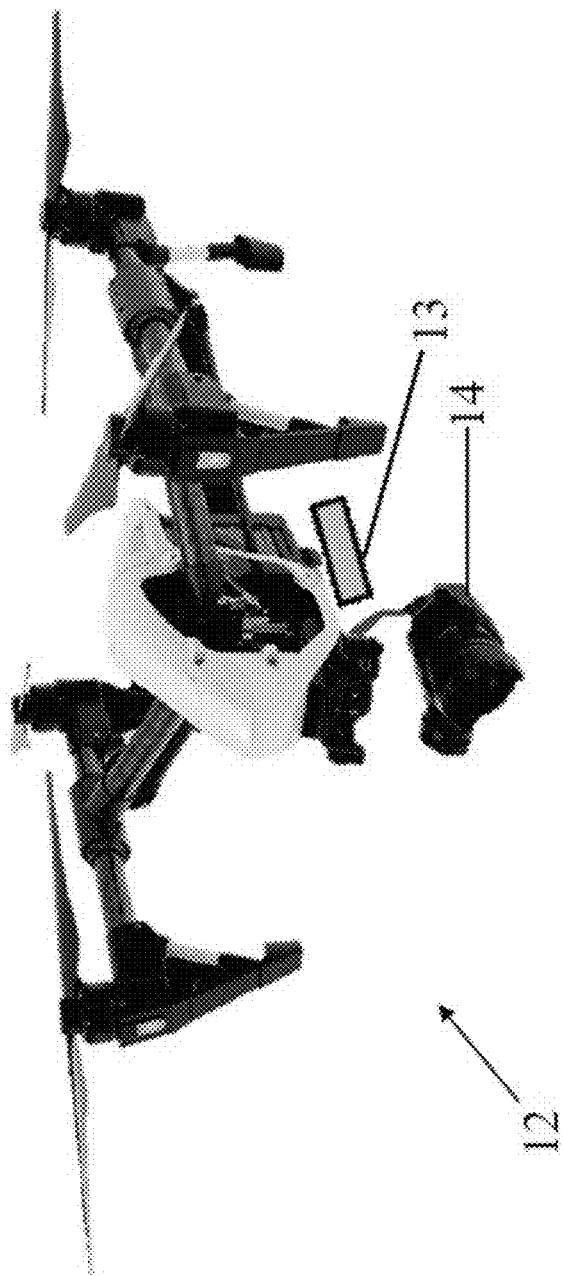
FIG. 1 is a perspective view of an unmanned aerial vehicle with lightweight sensors used in an air quality measurement system constructed according to the present invention.

In one embodiment of the present invention, an air quality measurement system is provided. Sensors capable of measuring temperatures, pressures and moisture content, as well as species concentrations of key compounds, are packaged together with associated electronics as sensor unit 13 and are mounted on an unmanned, low altitude aerial vehicle (UAV), such as shown in FIG. 1. The unmanned aerial vehicle 12 may take many different forms and may include a communications transmitter and an antenna. The unmanned aerial vehicle 12 may also include an optical sensor 14 in the form of a visible spectrum, IR spectrum, or multi-spectrum camera or camera arrays.

In one example, the UAV may be a copter based vehicle, such as that shown in FIG. 1. In another example, the UAV may be a fixed wing vehicle. The UAV will likely include a transmitter for flight control communications with the ground based pilot. In one example, the sensor unit 13 may have the sensor data piggy-backed on the UAV flight control communication. In another example, the sensor unit 13 may have a separate transmitter from the UAV flight control transmitter.

In one example, the UAV is constructed of a composite made from high temperature glass-ceramic matrices and inorganic polymers, such that it is capable of flying in high temperature and corrosive environment zones where local temperatures reach as high as 800K (980° F.), and may be as high as 1000K (1340° F.). The composite material is also resistant to deterioration due to attack from chemical species or compounds encountered.

The vehicle 12 may include a power source, such as a battery. The unmanned aerial vehicle 12 uses aerodynamic forces to provide vehicle lift and can be piloted remotely or fly autonomously. The UAV may include active cooling. One such example may include having an on-board liquid nitrogen tank (or other low-temperature compound) that can provide cooling as they undergo phase change during flight, In one non-limiting example, a plurality of electrically interconnected carbon nanotubes are mounted on a rigid substrate. A power source on the UAV (such as a battery) provides a substantially constant current to the electrically interconnected carbon nanotubes. The resistance or capacitance of the electrically interconnected carbon nanotubes is correlated to temperature, thereby providing a measurement of atmospheric temperature.

Likewise, changing pressure may result in a changing value of resistance for the electrically interconnected carbon nanotubes. These carbon nanotube sensors could likewise be connected to a monitor mounted on the UAV. Data from the sensors may be transmitted via a transmitter on the UAV wirelessly to a ground position controller 30.

Figure 2:
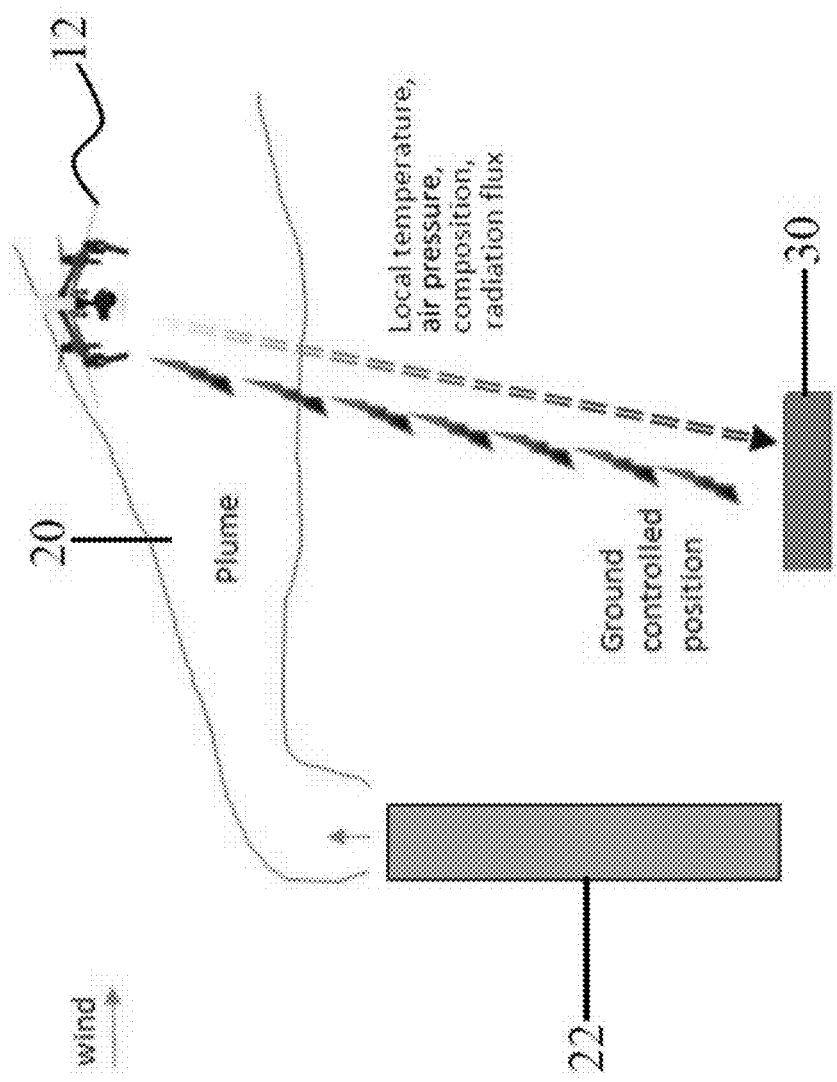
FIG. 2 is a simplified diagram illustrating a flare stack and emissions plume with the unmanned aerial vehicle with sensors shown in FIG. 1 of the present invention.

As best seen in FIG. 2, the UAV 12 can fly into a plume or plumes 20 above flares above a stack 22 or other large unconfined fires or emissions to monitor the temperatures, pressures, and moisture concentrations at various points inside, around, and above a plume 20, such as shown in FIG. 2. The UAV 12 with sensor unit 13 can fly many passes and trajectories through the plume using sensors to measure local temperature and relative humidity of the surrounding air, which data can be used to determine the edges of the plume while also recording the local temperatures and moisture concentrations in the plume, together with accurate three-dimensional location information, such as from, for example, a GPS system or combined GPS-RTK system. This feature allows the unmanned aerial vehicle to map contours of the plume and the downwind dispersion of the plume 20. Knowing the plume dispersion is useful for a variety of reasons, including (but not limited to) predicting the movement of the plume 20 as a function of wind and atmospheric condition to better locate ground mounted air sampling devices.

In another aspect of the invention, sensors capable of measuring gas species or compounds including, but not limited to, $CO_2$, CO, methane, and benzene, are included in the sensor unit 13 mounted on the UAV. In one non-limiting example, carbon nanotubes are associated with biological polymers, such as proteins, which can specifically and selectively bind to an analyte. In another example, the carbon nanotubes are associated with metal oxide coatings that provide selectivity in binding characteristics of different analytes. Using this selectivity, the presence and/or amount of gas species may thus be determined.

This measurement system combining a UAV 12 with the CNT equipped sensor unit 13 can fly into plumes above operating flares, other emission sources, or other large unconfined fires to monitor the real-time concentrations of these gases at various points inside, around, and above the plume 20, and the gas concentration data is correlated with accurate three-dimensional location information to provide accurate measures of combustion and destruction efficiencies at each location and mapping of hazardous regions. These measurements will have a variety of benefits. The multiplicity of locations where measurements are made can be used to provide an average value for the whole plume and may also be used to provide the average trajectory of the plume for early warning of potentially hazardous conditions. Measurements of combustion and destruction efficiencies will assist in determining compliance with governmental mandates, such as EPA consent decrees, worked out with large industrial flare operators.

Figure 3:
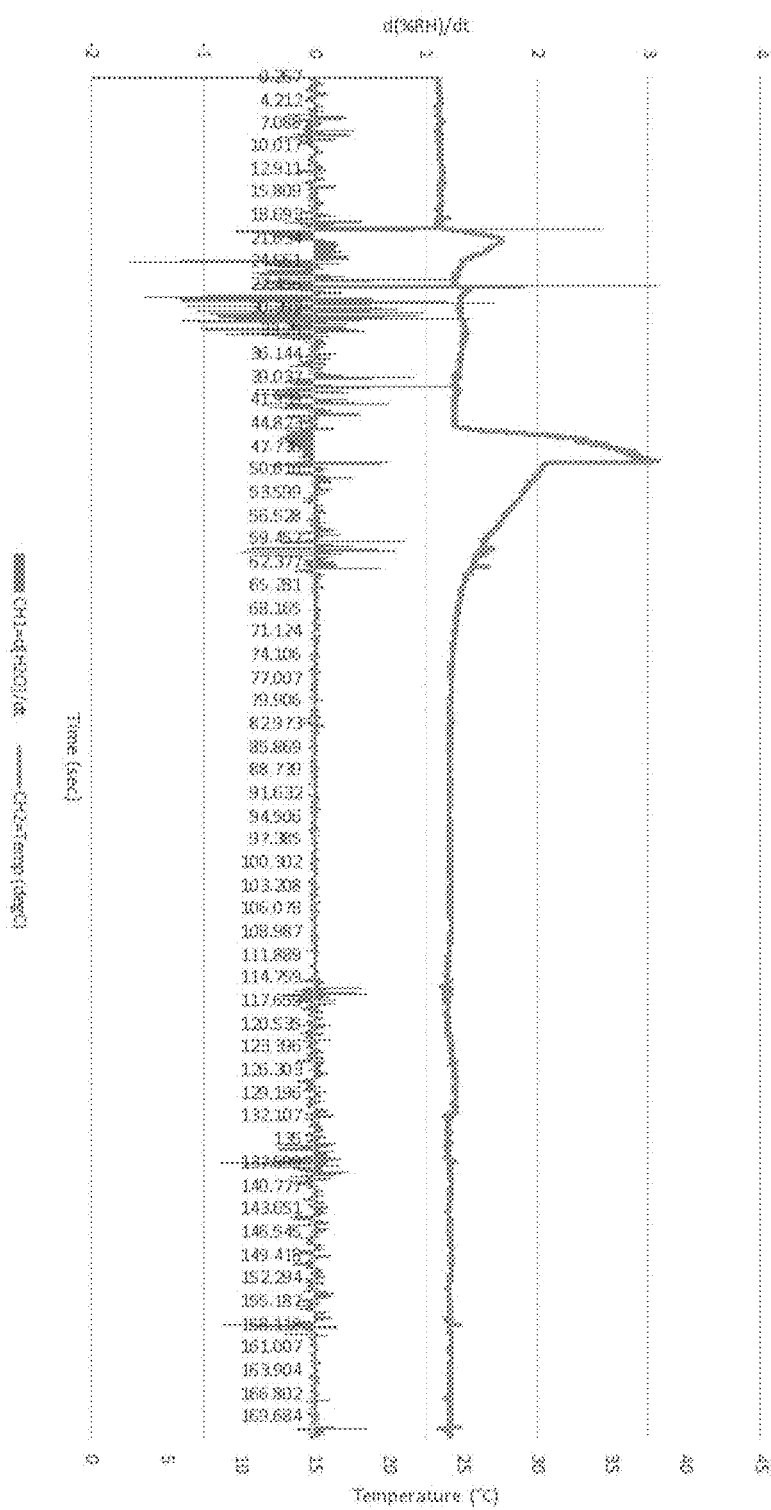
FIG. 3 is a chart illustrating readings or measurements of ambient air temperature and moisture content or humidity at various times.

FIG. 3 illustrates a chart or graph showing a series of data measurements charted against time. The time parameter is shown on the X axis. Measurement of ambient air temperature is shown at various times. Additionally, and separately, relative humidity measurements are shown at various times. The particular location of the unmanned aerial vehicle at the particular times can be linked together to determine the temperature and moisture content of the atmosphere at particular locations and times.

Similar measurements can be taken of gas species contents.

Accordingly, the contour of the plume 20 can be determined using the edge of the plume as defined by the transition point from atmospheric conditions of temperature and moisture concentration to conditions inside the plume where temperature and moisture concentrations are elevated. Using this plume contour, the dispersion of the plume 20, the direction of the plume, as well as speed of movement of the plume 20 for ongoing emission sources, can be determined.

Similar to the plume analysis using temperature and moisture outlined above, gas concentrations of combustion products or products of partial combustion, such as carbon monoxide and carbon dioxide, can be used to determine the plume contour. These gaseous concentrations may also be used to determine both combustion efficiency and destruction efficiency.

Whereas, the devices and methods have been described in relation to the drawings and claims, it should be understood that other and further modifications, apart from those shown or suggested herein, may be made within the spirit and scope of this invention.

What is claimed is:

1. An air quality measurement system, which comprises:
    an unmanned aerial vehicle;
    a plurality of electrically interconnected carbon nanotube sensors having gas sensitive metal oxide coatings for monitoring atmospheric air measurements, said plurality of sensors located on said aerial vehicle, wherein said plurality of sensors is configured to measure atmospheric chemicals selected from the group consisting of carbon monoxide, nitrogen dioxide, nitrogen oxide, sulfur dioxide, hydrogen sulfide, methane, and benzene;
    a monitor in communication with said plurality of sensors configured to receive said measurements, said monitor mounted on said aerial vehicle; and
    a transmitter in communication with said monitor, said transmitter mounted on said aerial vehicle.

2. An air quality measurement system as set forth in claim 1, including a ground position controller in wireless communication with said transmitter on said unmanned vehicle to receive data from said transmitter.

3. An air quality measurement system as set forth in claim 1, including multiple atmospheric air measurements from different locations at different elevations.

4. An air quality measurement system as set forth in claim 1, wherein said unmanned aerial vehicle is fabricated solely from high temperature glass-ceramic materials and inorganic polymers.

5. An air quality measurement system as set forth in claim 1, wherein said unmanned aerial vehicle is a remote controlled guided vehicle.

6. An air quality measurement system as set forth in claim 1, wherein said plurality of electrically interconnected carbon nanotube sensors is capable of monitoring atmospheric temperature.

7. An air quality measurement system as set forth in claim 1, wherein said plurality of electrically interconnected carbon nanotube sensors is capable of monitoring atmospheric pressure.

8. An air quality measurement system as set forth in claim 1, wherein said plurality of electrically interconnected carbon nanotube sensors is capable of monitoring atmospheric moisture.

9. An air quality measurement system as set forth in claim 1 wherein said sensors are probed with time dependent signals.

10. A method of measuring air quality, which method comprises:
    acquiring multiple atmospheric air measurements with a plurality of electrically interconnected carbon nanotube sensors having gas sensitive metal oxide coatings mounted on an unmanned aerial vehicle, wherein said plurality of sensors is configured to measure atmospheric chemicals selected from the group consisting of carbon monoxide, nitrogen dioxide, nitrogen oxide, sulfur dioxide, hydrogen sulfide, methane, and benzene;
    monitoring said atmospheric air measurements with a monitor in communication with said sensors;
    transmitting said multiple atmospheric air measurements from a transmitter on said unmanned aerial vehicle in communication with said monitor; and
    determining air quality from said multiple atmospheric air measurements.

11. A method as set forth in claim 10, wherein said multiple atmospheric air measurements are taken from different locations at different elevations at different times.

12. A method as set forth in claim 10, wherein said step of transmitting multiple atmospheric air measurements includes transmitting to a ground position controller.

13. A method as set forth in claim 10, wherein said unmanned aerial vehicle is fabricated solely from high temperature glass-ceramic materials and inorganic polymers.

14. An air quality measurement system, which comprises:
an unmanned aerial vehicle;
a plurality of electrically interconnected carbon nanotube sensors having biological polymers configured to bind an analyte for monitoring atmospheric air measurements, said plurality of sensors located on said aerial vehicle, wherein said plurality of sensors is configured to measure atmospheric chemicals selected from the group consisting of carbon monoxide, nitrogen dioxide, nitrogen oxide, sulfur dioxide, hydrogen sulfide, methane, and benzene;
a monitor in communication with said sensors configured to receive said measurements, said monitor mounted on said aerial vehicle; and
a transmitter in communication with said monitor, said transmitter mounted on said aerial vehicle.

15. An air quality measurement system as set forth in claim 14, wherein said unmanned aerial vehicle is fabricated solely from high temperature glass-ceramic materials and inorganic polymers.

* * * * *